(12) United States Patent
DiFoggio

(10) Patent No.: US 7,814,782 B2
(45) Date of Patent: Oct. 19, 2010

(54) DOWNHOLE GAS DETECTION IN DRILLING MUDS

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 62 days.

(21) Appl. No.: 11/837,991

(22) Filed: Aug. 13, 2007

(65) Prior Publication Data
US 2009/0044617 A1 Feb. 19, 2009

(51) Int. Cl.
*E21B 47/00* (2006.01)
(52) U.S. Cl. .................................................. 73/152.19
(58) Field of Classification Search ............... 73/152.04, 73/152.19, 152.46, 152.23, 152.25
See application file for complete search history.

(56) References Cited

U.S. PATENT DOCUMENTS

| | | | | |
|---|---|---|---|---|
| 3,776,032 A | * | 12/1973 | Vogel ........................ | 73/152.19 |
| 3,802,260 A | * | 4/1974 | Kishel ....................... | 73/152.04 |
| 3,824,167 A | * | 7/1974 | Oswin et al. ................ | 204/411 |
| 4,370,886 A | * | 2/1983 | Smith et al. ............... | 73/152.42 |
| 4,412,130 A | | 10/1983 | Winters | |
| 4,492,865 A | | 1/1985 | Murphy et al. | |
| 4,536,713 A | * | 8/1985 | Davis et al. ................. | 324/324 |
| 4,665,511 A | * | 5/1987 | Rodney et al. ................ | 367/35 |
| 5,351,532 A | * | 10/1994 | Hager ....................... | 73/152.55 |
| 6,244,096 B1 | * | 6/2001 | Lewis et al. ................... | 73/23.2 |
| 6,648,083 B2 | | 11/2003 | Evans et al. | |
| 6,768,106 B2 | | 7/2004 | Gzara et al. | |
| 2004/0045350 A1 | * | 3/2004 | Jones et al. ............... | 73/152.23 |
| 2005/0205256 A1 | | 9/2005 | DiFoggio | |
| 2005/0241382 A1 | * | 11/2005 | Coenen .................... | 73/152.19 |
| 2006/0016592 A1 | | 1/2006 | Wu | |
| 2006/0032301 A1 | * | 2/2006 | DiFoggio ................. | 73/152.18 |
| 2007/0144740 A1 | | 6/2007 | Guo et al. | |

FOREIGN PATENT DOCUMENTS

WO WO 9634285 10/1996

OTHER PUBLICATIONS

Brumboiu, A.O. et al., "Application of Semipermeable Membrane Technology in the Measurement of Hydrocarbon Gases in Drilling Fluids," 2000 SPE/AAPG Western Regional Meeting, Jun. 19-23, 2000, pp. 1-12, Long Beach, California.

* cited by examiner

*Primary Examiner*—John Fitzgerald
(74) *Attorney, Agent, or Firm*—Cantor Colburn LLP

(57) ABSTRACT

Apparatus and method are disclosed for detecting gas in return fluids. A semi-permeable interface is disposed on a tool sub, the semi-permeable interface being in communication with a fluid cell and with a return fluid in an annular region defined by an outside the tool sub and a borehole wall. A sensor responsive to a gas carried by the return fluid is disposed in the fluid cell to sense the gas that enters the fluid cell from the return fluid via the semi-permeable interface.

24 Claims, 3 Drawing Sheets

DOWNHOLE GAS DETECTION IN DRILLING MUDS

BACKGROUND

1. Technical Field

The present disclosure generally relates to well bore tools and in particular to apparatus and methods for conducting downhole operations.

2. Background Information

Oilfield wellbores are formed by rotating a drill bit carried at an end of a drill string. A typical drill string includes a tubing, which may be drill pipe made of jointed sections or a continuous coiled tubing, and a drilling assembly that has a drill bit at its bottom end. The drill bit is rotated by a mud motor carried by a drilling assembly carried on the drill string and/or by rotating the drill pipe. Drilling fluid, also referred to as the "mud," is pumped under pressure through the tubing from a source called a mud pit located at the surface. The drilling fluid exits the tubing through a drill bit and returns to the surface by flowing upward in an annulus between the tubing and the borehole wall. The drilling fluid is usually a combination of solids, water and various additives selected to adjust the density and chemical characteristics of the drilling fluid.

The drilling fluid serves to lubricate and cool downhole drilling components such as the drill bit. The drilling fluid also serves, when in the annulus as a return fluid, to clean the borehole by carrying cuttings to the surface and to provide hydrostatic pressure against the borehole wall. The composition and density of the drilling fluid in conjunction with the depth of the borehole determine the hydrostatic pressure. The pressure exerted against the borehole wall is usually kept higher than the formation pressure to form a pressure overbalance. The overbalance helps prevent borehole collapse and helps to keep formation fluids from entering the annulus.

Any change in the drilling fluid composition that substantially reduces the density of the fluid may cause the hydrostatic pressure to fall below the formation pressure and allow fluids to enter the well bore. Some fluids entering the borehole may cause corrosion to downhole tools. Left uncontrolled, the entering fluids may cause a "kick", which is an upward thrust of fluids from the annulus. Such "kicks" can cause equipment damage, damage to the well, environmental concerns, and pose serious safety hazards for personnel at the well site. In some cases, the kick is a result of drilling into a zone of unexpectedly high formation pressure. Kick may also be the result of washout due to unstable formations. In other cases, gases produced from formations quickly reduce return fluid density.

Of course, even while drilling at hydrostatic pressures that exceed the formation fluid pressure, any pore fluids that had once been part of the wellbore rock will become mixed in the drilling fluid. Although this small amount of pore fluid is unlikely to cause any significant change in drilling fluid density, knowing its composition is still very useful information. For example, return fluid containing considerable methane is an indication that a gas zone has been penetrated by the drilling. If the return fluid contains carbon dioxide, certain corrosion inhibiters may be needed in the drilling fluid. Hydrogen sulfide in the return fluid may indicate a need to add scavenging agents to protect both equipment and personnel. For the long term, we also gain more information about the reservoir that helps when planning the minimum required corrosion resistance of materials to be used in the production facilities and when estimating the economic value of the produced hydrocarbons. Hydrocarbons that contain very high levels of carbon dioxide or more than trace amounts of hydrogen sulfide are discounted by what it costs to remove them.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

Disclosed is an apparatus for detecting gas in return fluids. The apparatus includes a semi-permeable interface disposed on a tool sub, the semi-permeable interface being in communication with a fluid cell and with a return fluid in an annular region defined by an outside the tool sub and a borehole wall. A sensor responsive to a gas carried by the return fluid is disposed in the fluid cell to sense the gas that enters the fluid cell from the return fluid via the semi-permeable interface.

In another aspect, a method for detecting a gas in return fluid includes placing a semi-permeable interface disposed on a tool sub in communication with a fluid cell and with a return fluid in an annular region defined by an outside the tool sub and a borehole wall, and sensing a return fluid gas that enters the fluid cell from the return fluid via the semi-permeable interface using a sensor responsive to the return fluid gas, the sensor being disposed in the fluid cell.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals and wherein.

DESCRIPTION OF EXEMPLARY EMBODIMENTS

The present disclosure uses terms, the meaning of which terms will aid in providing an understanding of the discussion herein. Drilling fluid refers to fluid pumped primarily through a drill string toward a drill bit, and "return fluid" refers to annular fluid returning toward the surface of a well borehole. Return fluid will typically include drilling fluid contaminated by cuttings generated by a drill bit and by formation pore fluids. For the purpose of this disclosure, the term "kick" means any unscheduled entry of formation fluid into the borehole. The term "semi-permeable" used herein means substantially permeable by a gas or vapor and substantially impermeable by liquids and particulates.

Figure 1:
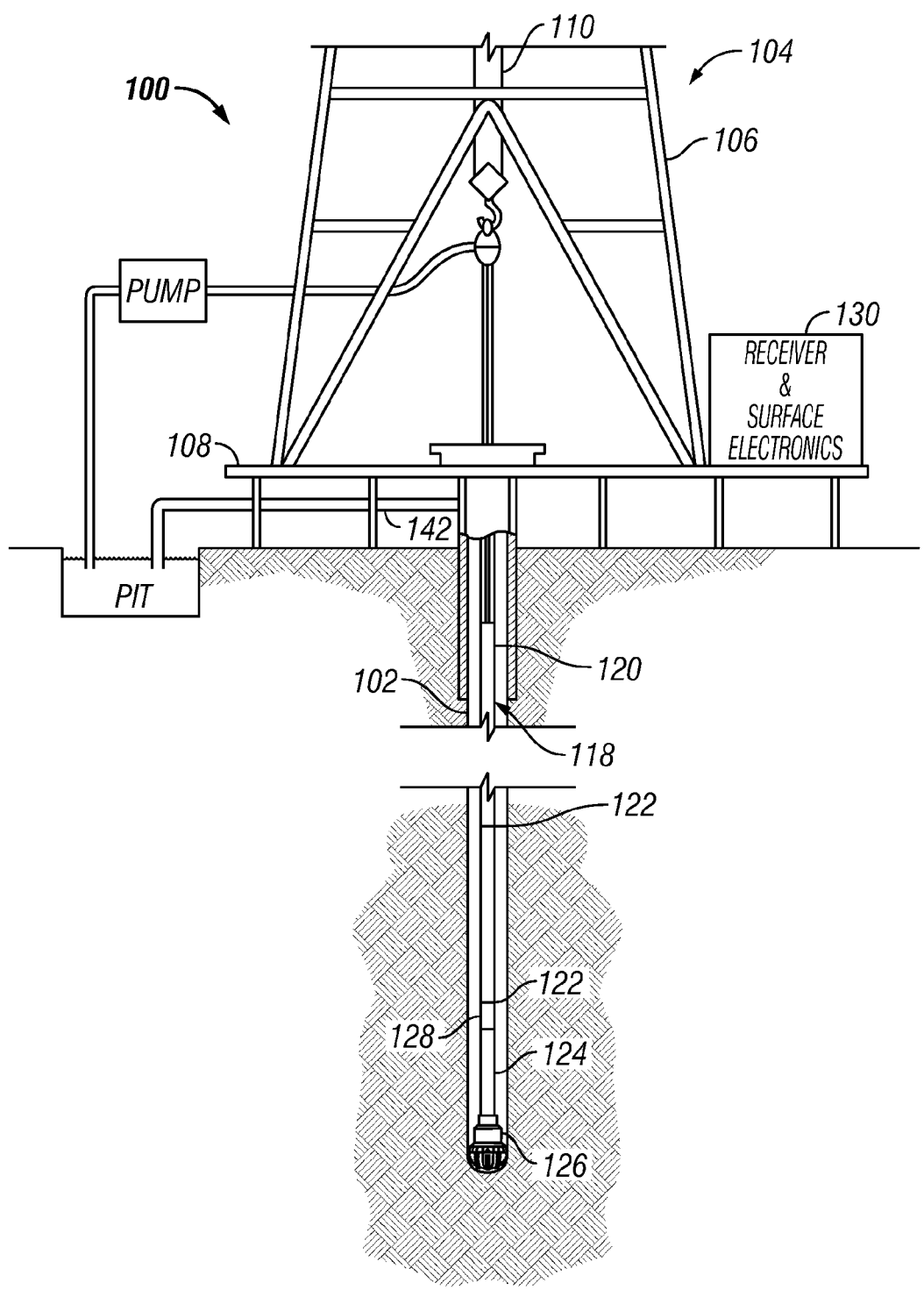
FIG. 1 is an elevation view of a drilling system.

FIG. 1 shows an elevation view of a non-limiting exemplary simultaneous drilling and logging system 100 that may be used in several embodiments of the present disclosure. A well borehole 102 is shown drilled into the earth under control of surface equipment including a drilling rig 104. In accordance with a conventional arrangement, the drilling rig 104 may include a derrick 106, a derrick floor 108, draw works 110, and a drill string 118. The drill string 118 may include any of several typical drill pipe 120 configurations. In several examples the drill pipe 120 may be a jointed pipe or coiled tube. In the particular example shown, pipes are joined in a conventional manner such as threaded pipe joints 122, which are sometimes called collars. A bottom hole assembly (BHA) 124 is shown located down hole on the drill string 118 near a drill bit 126.

The BHA 124 may carry a processor and any number of sensors (not separately shown) for measuring formation and drilling parameters downhole. A transmitter 128 may be carried by the BHA 124, but may be below or above the BHA 124. The transmitter 128 receives information in the form of signals from the sensors or processor and converts the information for transmitting in a desired medium. For example, the transmitter 128 may transmit information in the form of acoustic energy using the drill string 118 as a transmission medium, the transmitter 128 may be a mud pulse generator for using drilling fluid or return fluid as the transmission medium, or the transmitter 128 may transmit via wires in the case of wired pipe drill strings. A receiver 130 may be located at a suitable surface location for receiving the information transmitted by the transmitter 124.

A pump located at a surface location pumps drilling fluid from a surface mud pit into the drill string 118. The drilling fluid flows through the drill string 118 toward a drill bit 126 to lubricate and cool various tools carried by the drill string and to power downhole components, such as a drill motor, a turbine pump, or downhole generator. The drilling fluid returns to the surface as return fluid, and the return fluid is filtered and returned to the pit via a suitable pipe.

Figure 2:
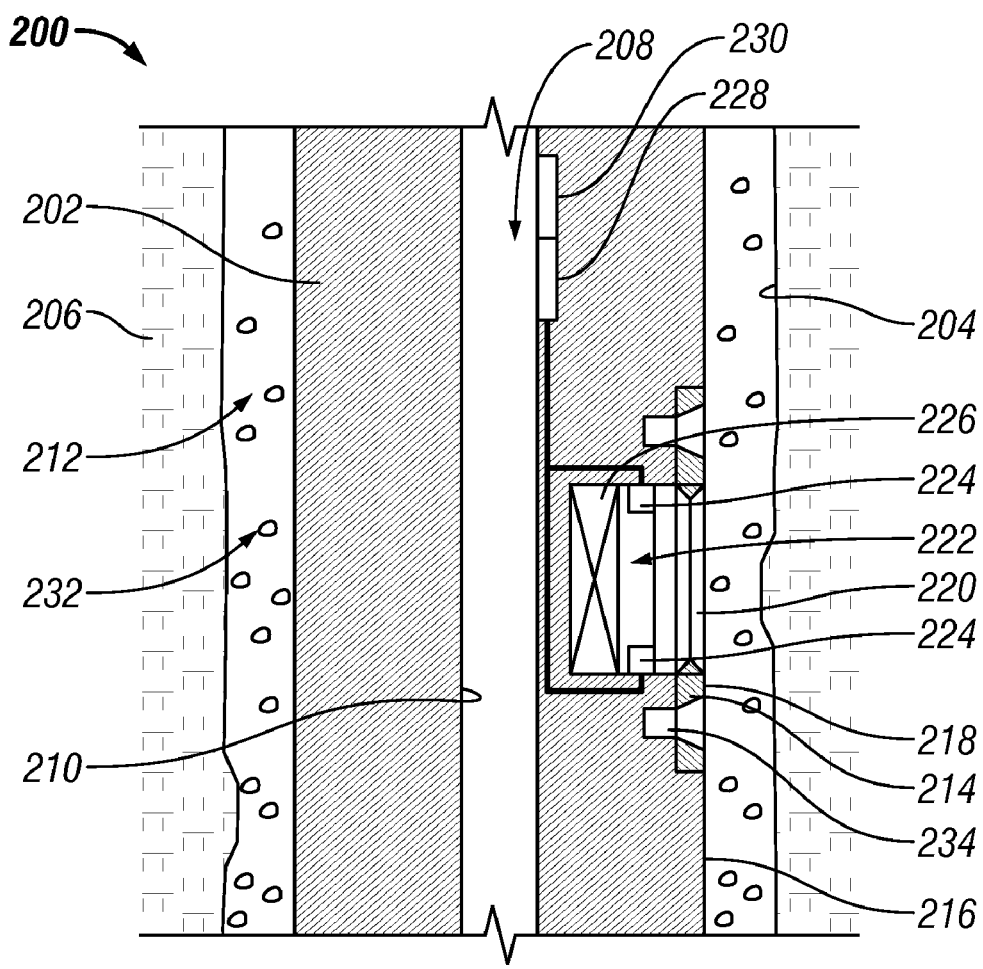
FIG. 2 illustrates a non-limiting example of a tool sub that may be used in a drilling system such as the system of FIG. 1.

FIG. 2 is a cross section elevation view of a tool 200 portion according to one example of the disclosure. The tool 200 shown in FIG. 2 includes a drilling sub 202 within a well borehole 204 adjacent a subterranean formation 206. The tool 200 may be included in a while-drilling system, such as the system 100 described above and shown in FIG. 1. As noted above with reference to FIG. 1, drilling fluid 208 is pumped toward a drill bit 126 (FIG. 1) through a central bore 210 of the tool 200. Return fluid 212 is shown in the borehole annulus returning toward the surface. The return fluid 212 is shown carrying cuttings 232 toward the surface. While the figure shows a vertically-oriented tool 200, the tool 200 in practice may be in a deviated well borehole having any of a number of angular inclinations. Therefore, any statement herein as to directionality is merely for illustration and not by way of limiting the disclosure.

Continuing with FIG. 2, the cuttings 232 are bits of the formation 206 disintegrated by the drill bit 126. Where a particular formation structure includes formation fluid, the disintegration of the formation produces the formation fluid along with the cuttings 232. This form of formation fluid production will exist even with properly overbalanced hydrostatic pressure. The formation fluid produced with the cuttings may be a multi-phase fluid containing liquids and gases, and the production of gas may reduce return fluid density.

A gas detector 214 for detecting gas in the return fluid 212 is disposed in a wall 216 of the drilling sub 202. The gas detector 214 shown includes a plate 218, a semi-permeable interface 220 between a fluid cell 222 and the borehole return fluid 212, and one or more gas sensors 224 positioned within the fluid cell 222 and near the semi-permeable interface 220. A trap 226 having a high surface area trapping material may be positioned within the fluid cell 222. The gas sensors 224 may be electrically connected to a downhole processor 228 for processing information received from the gas sensors 224.

The processor 228 is shown in communication with a transmitter 230. The transmitter may be used in similar fashion to the transmitter 128 described above and shown in FIG. 1 to transmit processed information to the surface or to another location in the drill string.

The drilling sub wall 216 may be machined to receive the gas detector 214. Suitable fasteners 234 may be used to secure the plate 218 to the drilling sub 202. The fasteners 234 may be threaded fasteners or any other suitable fasteners. In another embodiment, the drilling sub wall 216 may be machined with threads to receive a gas detector having an externally threaded case. In several embodiments, the gas detector 214 is readily detachable from the drilling sub 202 to allow for changing the detector 214 or for removing or replacing the trap 226 and or the semi-permeable interface 220.

The fluid cell 222 in several embodiments may be a small volume that may be filled with air or other substantially inert gas. The volume may be initially pressurized to any of a range of pressure that will be less than downhole pressure. A standard atmosphere may be used. In other embodiments, the volume may initially be at a pressure below a standard atmosphere or may be evacuated.

The trap 226 may be positioned within the fluid cell 222 to remove a gas or vapor from the sensor portion of the fluid cell 222. The trapping material of the trap 226 may be any material suitable for removing the gas being sensed from the fluid cell. Its purpose is to reduce the concentration of the gas being sensed to background levels during periods when that gas is not entering the fluid chamber through the membrane in contact with the drilling fluid, thus regenerating the fluid cell. For example, the material may be an adsorbent or an absorbent material. In one example the trap 226 is position within the fluid cell 222 farther from the semi-permeable interface 220 than are the gas sensors 224. The trapping material may be activated charcoal or other activated carbon to adsorb the gas that enters the fluid cell 222 to reduce gas accumulation. Alternatively, the sensor may be operated as a cumulative sensor. That is, it could report the rate of change of the concentration of the gas of interest as that gas keeps accumulating within the fluid cell as would occur when no gas trap is used. In some cases a downhole pump (not shown) may be used to reduce pressure in the fluid cell 222 or to remove gas from the sensor portion of the fluid cell 222.

In several embodiments, the semi-permeable interface 220 may be perm-selective meaning that the permeability of the semi-permeable interface is permeable to only a selected gas of interest or to a selected set of gases of interest. Typical gases encountered when drilling through fluid-producing formations include, for example, methane, carbon dioxide, hydrogen sulfide and nitrogen. The semi-permeable interface 220 may be constructed to allow only one or more of these gases to permeate the semi-permeable interface. Selecting known potentially significant gases may help in the early detection of a potential kick or in early detection of a potential corrosion or health problem and may help avoid erroneous readings.

Still referring to FIG. 2, the gas sensor or sensors 224 may be any suitable detector for sensing gas in the fluid cell 222 to estimate whether gas is entering the fluid cell 222. In one embodiment, the detector may include a small metal oxide sensing element. Exemplary metal oxide detectors may include oxides such as tin oxide, tungsten oxide, zirconium oxide, and the like. In one embodiment, the gas sensor 224 includes a metal oxide detector that is a semiconductor-based detector with an electrical conductivity that changes with the concentration of a reactive gas. The conductivity may change in several ways, and may include a logarithmic change in the conductivity. The sensing element of such devices may be small (about an eighth inch square) and is generally electrically heated to 400 degrees Celsius during normal operation, which is higher than downhole temperatures. Therefore, the sensor can operate at downhole temperatures and does not require cooling, which would add complexity. One can simply supply less electrical energy to heat the sensor to 400 C when it is starts at the hot, ambient, downhole temperature. Metal oxide gas sensors are available in small TO-5 cans that are about ⅜ of an inch (0.97 cm) in diameter and less than ¼ of an inch (0.64 cm) tall. Chemical Field Effect Transistors (ChemFETs) might also be used but they may require cooling as they generally are not rated to operate above 100 C and borehole temperatures can, in some cases, exceed 200 C. In several embodiments, the gas sensor 224 is sensitive to one or more selected gases. Examples of gases that may be selectively detected by the gas sensor 224 include, but are not limited to, $CH_4$, $H_2S$, $CO_2$, CO, $H_2$, $NH_3$, $O_2$, or other gases. In one embodiment, the gas sensor 224 is responsive to several gases. Several combinations of the gas sensor 224 and semi-permeable interface 220 may be used depending on whether one or more particular gases are to be detected. For example, the semi-permeable interface 220 may be permeable to several gases and the detector may be gas specific, e.g. responsive to a selected gas. In another example, the gas sensor 224 may be responsive to several gases and the semi-permeable interface may be perm-selective. In another example, several gas sensors 224 may each separately detect a single gas of interest.

Figure 3:
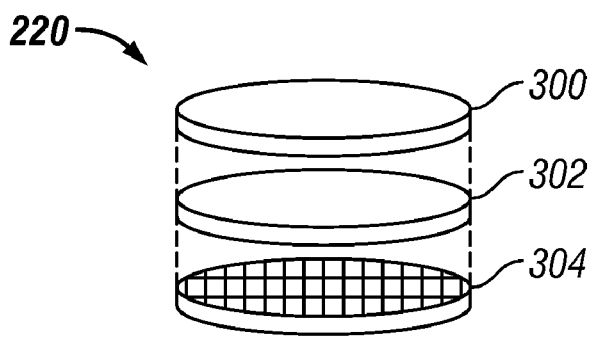
FIG. 3 is a non-limiting example of a semi-permeable interface according to several embodiments.

Referring to FIGS. 2 and 3, in one embodiment, the semi-permeable interface 220 may include a semi-permeable membrane 300. A semi-permeable membrane 300 is generally considered to be impermeable to liquids, while permeable to gases. The membrane 300 may be coupled to a porous support structure 302, and the support structure 302 may be coupled to a porous reinforcement layer 304. The multi-layer structure provides sufficient permeability and can withstand the pressure differential across the semi-permeable interface 220 without adverse deformation.

The membrane may be any suitable semi-permeable material. In several embodiments, the membrane 300 may include a layer of a natural polymer and/or a synthetic polymer. In one embodiment, the membrane may include a layer of silicone rubber. In other embodiments, the semi-permeable interface 220 may include a hard glassy polymer as a membrane 300 material. In several embodiments, the hard glassy polymer may be a high free volume glassy polymer such as polymethylpentene (PMP) that increases gas permeability and gas selectivity. In another example, a perfluoroalkoxy fluorocarbon resin can be used for high chemical resistance.

The support structure 302 may be any suitable porous support structure. In one example, the support structure is a sintered metal structure. The reinforcement layer 304 may be any suitable layered material that provides sufficient reinforcement for the semi-permeable interface 220, while protecting against pressure-induced deformation. In one example, the reinforcement layer 304 is a metal plate having one or more holes extending through the plate. A face of the plate may include scoring between the holes. The plate may be any suitable, and in one example, the plate is stainless steel. The layered semi-permeable interface 220 according to the example of FIG. 3 need not be planar as shown. The semi-permeable interface may be formed in other shapes depending on particular desired tool configurations. One example will be discussed later in reference to FIG. 4.

In operation, a tool 200 is conveyed into a well borehole 204 on a drill string 118. Gas flowing in the return fluid 212 permeates through the semi-permeable interface 220 driven by the difference in concentration of a selected gas across the semi-permeable interface 220. Where the concentration outside the semi-permeable interface and the concentration inside the fluid cell 222 of a particular gas are different, the gas will diffuse through the semi-permeable interface at a rate that is generally proportional to the concentration gradient. The gas sensor 224 that is responsive to the gas entering the fluid cell 222 will convey an electrical signal to the processor 228. Where the gas poses a potential risk for a kick, the transmitter 230 may transmit information relating to the detected gas to the surface for prompt action by surface operators. For example, the mud engineer may use the early information to adjust drilling fluid density in view of the detected gas. In another example, the drilling operator may determine, based in part on the type of gas detected, to change out one or more drilling components, change drilling speed, weight on bit, drilling fluid pump rate, or other suitable action.

Figure 4:
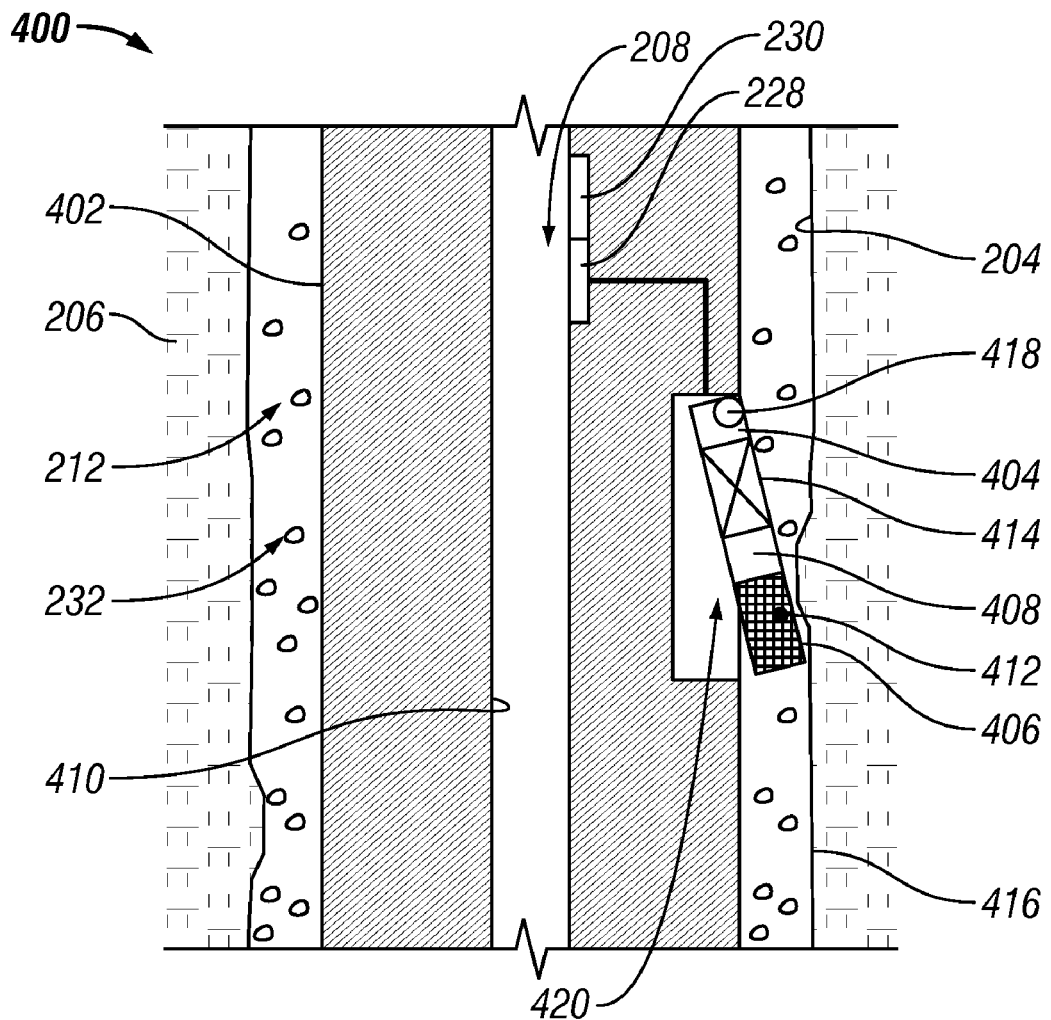
FIG. 4 is another non-limiting example of a tool sub that may be used in a drilling system such as the system of FIG. 1.

FIG. 4. is an example of a while-drilling tool with a gas detector that extends from a drilling sub. Shown is a cross section elevation view of a tool 400 portion according to one example of the disclosure. The tool 400 shown in FIG. 4 includes a drilling sub 402 within a well borehole 204 adjacent a subterranean formation 206. The tool 400 may be included in a while-drilling system, such as the system 100 described above and shown in FIG. 1. Similar to the embodiments described above and shown in FIG. 2, drilling fluid 208 is pumped toward a drill bit 126 (FIG. 1) through a central bore 410 of the tool 400. Return fluid 212 is shown in the borehole annulus returning toward the surface. The return fluid 212 is shown carrying cuttings 232 toward the surface and may include one or more gases as discussed above with reference to FIG. 2.

In the example of FIG. 4, a gas detector 420 for detecting gas in the return fluid 212 is disposed on an extendable element 404 shown extended from a wall 416 of the drilling sub 402. The gas detector 420 shown includes a semi-permeable interface 406 on the extendable element such that extending the element 404 will carry the semi-permeable interface 406 into the annulus and into the return fluid 212 flow path. One or more gas sensors 412 are positioned within a fluid cell 408 located within the extendable element 404 and near the semi-permeable interface 406. A high surface area trapping material 414 may be positioned within the fluid cell 408. The gas sensors 412 may be electrically connected to a downhole processor 228 for processing information received from the gas sensors 224. The processor 228 is shown in communication with a transmitter 230. The transmitter may be used in similar fashion to the transmitter 128 described above and shown in FIG. 1 to transmit processed information to the surface or to another location in the drill string 118 (FIG. 1).

Suitable connections 418 mat be used to movably fasten the extendable element 404 to the drilling sub 402. Where the extendable element is rotated for extension as shown, the fastener may be a pivoting fastener. In other embodiments, the extendable element 404 may be a piston-type extension element. In other embodiments, a fixed extended element may be used instead of the extendable element 404. In one example, the gas detector 420 may be mounted in a centralizer or stabilizer blade. In several embodiments, the gas detector 420 is readily detachable from the drilling sub 402 to allow for changing the gas detector 420 or for removing or replacing the trap 414 and or the semi-permeable interface 406.

The fluid cell 408 in several embodiments may be a small volume that may be filled with air or other substantially inert gas. The volume may be initially pressurized to any of a range of pressure that will be less than downhole pressure. A standard atmosphere may be used. In other embodiments, the volume may initially be at a pressure below a standard atmosphere or may be evacuated. The trap 414 may have a high surface area trapping material that is positioned within the fluid cell 408 to remove gas from the sensor portion of the fluid cell 408. The trapping material may be any material suitable for removing a gas. For example, the material may be an adsorbent or an absorbent material. The trapping material may be activated charcoal or other activated carbon material may be used to adsorb the gas that enters the fluid cell 408 to reduce gas accumulation. In some cases a downhole pump (not shown) may be used to reduce pressure in the fluid cell 408 or to remove gas from the sensor area of the fluid cell 408.

In several embodiments, the semi-permeable interface 406 may be perm-selective meaning that the permeability of the semi-permeable interface is permeable to only a selected gas of interest or to a selected set of gases of interest. The semi-permeable interface 406 may be constructed to allow only one or more of these gases to permeate the semi-permeable interface. Selecting known potentially harmful gases may help in the early detection of a potential kick and may help avoid erroneous readings.

The gas sensor or sensors 412 may be any suitable sensor for sensing gas in the fluid cell 408 to estimate whether a particular gas of interest is entering the fluid cell 408. In one embodiment, the sensor may include a small metal oxide sensing element. Exemplary metal oxide detectors may include oxides such as tin oxide, tungsten oxide, zirconium oxide, and the like. In one embodiment, the gas sensor 412 includes a metal oxide detector that is a semiconductor-based detector with an electrical conductivity that changes with the concentration of a reactive gas. The conductivity may change in several ways, and may include a logarithmic change in the conductivity. In several embodiments, the gas sensor 412 is sensitive to one or more selected gases. Examples of gases that may be selectively detected by the gas sensor 412 include, but are not limited to, $CH_4$, $H_2S$, $CO_2$, $CO$, $H_2$, $NH_3$, $O_2$, or other gases. In one embodiment, the gas sensor 412 is responsive to several gases. Several combinations of the gas sensor 412 and semi-permeable interface 406 may be used depending on whether one or more particular gases are to be detected. For example, the semi-permeable interface 406 may be permeable to several gases and the detector may be gas specific, e.g. responsive to a selected gas. In another example, the gas sensor 412 may be responsive to several gases and the semi-permeable interface is perm-selective. In another example, several gas sensors 412 may each separately detect a single gas of interest.

The semi-permeable interface 406 may include a layered construction such as the semi-permeable interface 220 described above and shown in FIGS. 2 and 3. In the present example, a layered construction may be used where the semi-permeable interface is fitted to the extendable element. In one example, the layered semi-permeable interface may be constructed in a helical fashion that is then mounted on the extendable element 404.

The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, use of equivalent functional couplings for couplings described herein, and/or use of equivalent functional actions for actions described herein. Such insubstantial variations are to be considered within the scope of the claims below.

What is claimed is:

1. A downhole apparatus for detecting return fluid gas, the apparatus comprising:
    a semi-permeable interface disposed on a tool sub, the semi-permeable interface being in communication with a fluid cell and with a return fluid in an annular region defined by an outside the tool sub and a borehole wall, the fluid cell configured to be maintained at a pressure in a range of above a vacuum pressure to about one atmosphere; and
    a metal oxide sensor responsive to a gas carried by the return fluid, the sensor being disposed in the fluid cell to sense the gas that enters the fluid cell from the return fluid via the semi-permeable interface.

2. An apparatus according to claim 1, wherein the sensor is responsive to one or more of methane, carbon dioxide, hydrogen sulfide and nitrogen.

3. An apparatus according to claim 1 further comprising a member that extends from the tool sub into the annular region, wherein the semi-permeable interface is disposed on the member.

4. An apparatus according to claim 1, further comprising a downhole transmitter that transmits a signal to a surface location, the signal being indicative of gas presence in the return fluid.

5. An apparatus according to claim 1, wherein the semi-permeable interface comprises a gas-selective material that is permeable to one or more selected gases.

6. An apparatus according to claim 5, wherein the one or more selected gases include at least one of methane, carbon dioxide, hydrogen sulfide and nitrogen.

7. An apparatus according to claim 1, wherein the semi-permeable interface comprises a plurality of layers, the plurality of layers including a structural support layer, reinforcement layer and a semi-permeable membrane layer.

8. An apparatus according to claim 7, wherein the structural support layer comprises a sintered metal filter, and the reinforcement layer comprises a pressure plate including a metal plate having a plurality of holes to provide gas communication across the semi-permeable membrane.

9. An apparatus according to claim 1, wherein the semi-permeable interface comprises a glassy polymer.

10. An apparatus according to claim 9, wherein the glassy polymer includes one or more of a polymethylpentene and a perfluoroalkoxy fluorocarbon resin.

11. An apparatus according to claim 1, wherein the semi-permeable interface comprises a semi-permeable membrane.

12. An apparatus according to claim 11, wherein the semi-permeable membrane includes a layer of at least one of a natural polymer and a synthetic polymer.

13. An apparatus according to claim 11, wherein the semi-permeable membrane includes a layer of silicone rubber.

14. An apparatus according to claim 1, further comprising a trap positioned within the fluid cell to remove at least some of the return fluid gas from the fluid cell.

15. An apparatus according to claim 14, wherein the trap comprises an activated carbon material.

16. A method for downhole return fluid gas detection comprising:
    placing a semi-permeable interface disposed on a tool sub in communication with a fluid cell and with a return fluid in an annular region defined by an outside of the tool sub and a borehole wall;
    maintaining the fluid cell at a pressure in a range of above a vacuum pressure to about one atmosphere; and
    sensing a return fluid gas that enters the fluid cell from the return fluid via the semi-permeable interface using a metal oxide sensor responsive to the return fluid gas, the sensor being disposed in the fluid cell.

17. A method according to claim 16 further comprising extending a member from the tool sub into the annular region, wherein the semi-permeable interface is disposed on the member.

18. A method according to claim 16, further comprising transmitting a signal to a surface location, the signal being indicative of gas presence in the return fluid.

19. A method according to claim 16, further comprising removing at least some of the return fluid gas from the fluid cell using a trap positioned within the fluid cell.

20. A method according to claim 16, wherein the trap comprises an activated carbon material.

21. A method according to claim 16, further comprising allowing only one or more selected gases to enter the fluid cell using a gas-selective material in the semi-permeable interface, the gas-selective material being permeable to the one or more selected gases.

22. A method according to claim 21, wherein the one or more selected gases include at least one of methane, carbon dioxide, hydrogen sulfide and nitrogen.

23. A method according to claim 16, wherein the sensor is responsive to one or more of methane, carbon dioxide, hydrogen sulfide and nitrogen.

24. A method according to claim 23, wherein the sensor includes a metal oxide element.

* * * * *